(12) United States Patent
Greenburg

(10) Patent No.: US 9,138,341 B2
(45) Date of Patent: Sep. 22, 2015

(54) DENTAL APPLIANCE

(76) Inventor: Jonathan Gil Greenburg, Calabasas, CA (US)

( * ) Notice: Subject to any disclaimer, the term of this patent is extended or adjusted under 35 U.S.C. 154(b) by 167 days.

(21) Appl. No.: 13/507,707

(22) Filed: Jul. 20, 2012

(65) Prior Publication Data

US 2013/0112208 A1 May 9, 2013

Related U.S. Application Data

(63) Continuation of application No. 12/317,933, filed on Dec. 30, 2008, now abandoned.

(60) Provisional application No. 61/009,693, filed on Dec. 31, 2007, provisional application No. 61/123,849, filed on Apr. 11, 2008.

(51) Int. Cl.
A61F 5/56 (2006.01)

(52) U.S. Cl.
CPC ..................................... A61F 5/566 (2013.01)

(58) Field of Classification Search
USPC ............ 128/848, 859–862; 433/6–7; 602/902
See application file for complete search history.

(56) References Cited

U.S. PATENT DOCUMENTS

| | | | | |
|---|---|---|---|---|
| 6,766,802 B1* | 7/2004 | Keropian | | 128/848 |
| 2007/0028926 A1* | 2/2007 | Kotani | | 128/848 |
| 2008/0053463 A1* | 3/2008 | Enoch | | 128/861 |
| 2009/0120448 A1* | 5/2009 | Keropian | | 128/848 |
| 2010/0043804 A1* | 2/2010 | Razmovski | | 128/848 |

* cited by examiner

Primary Examiner — Ophelia A Hawthorne
(74) Attorney, Agent, or Firm — Steven E. Shapiro

(57) ABSTRACT

The present invention is a dental oral appliance to open the airway for a sleeping individual who suffers with snoring or obstructive sleep apnea. The appliance includes a base to secure the appliance within the mouth for the individual. Typically, the base will fit over and secure to the lower teeth of the individual. The appliance also includes a tongue restraining device connected to the base. The tongue restraining device has a substantial breach formed therein to permit movement of the tongue so that the user can more easily swallow saliva. A ramp might also be attached to the anterior portion of the base to advance the mandible.

10 Claims, 4 Drawing Sheets

DENTAL APPLIANCE

CROSS-REFERENCE TO RELATED APPLICATIONS

This application is a continuation of U.S. patent application Ser. No. 12/317,933 filed on Dec. 30, 2008 now abandoned and entitled "Dental Appliance", which in turn claims benefit of U.S. Provisional Patent Application No. 61/009,693 (filed Dec. 31, 2007) and U.S. Provisional Patent Application No. 61/123,849 (filed Apr. 11, 2008). The specifications of said provisional patent applications are incorporated herein by this reference as though set forth in full.

STATEMENT REGARDING FEDERALLY SPONSORED RESEARCH OR DEVELOPMENT

Not Applicable

FIELD OF INVENTION

The present invention relates to dental appliances for the treatment of snoring.

BACKGROUND OF THE INVENTION

Medical studies have shown that snoring can have serious medical consequences for people. Many people who snore suffer from Obstructive Sleep Apnea. If not diagnosed or if left untreated, Obstructive Sleep Apnea can result in severe medical consequences such as systemic high blood pressure, cardiovascular disease, stroke and heart attack.

Spouses also suffer through the night from the noise of the snorer. Snoring not only disturbs the sleeping pattern of the snorer, it is also disruptive to his or her spouse. This leaves both unrefreshed, tired and sleepy throughout the day. It can cause sleepiness while driving, reading, working or doing other tasks.

A broad variety of intra-oral and dental appliances and devices are now available to treat a patient for snoring. However, most of these are uncomfortable to the user and studies have shown that the vast majority of these devices go unused. Other treatments for snoring include various surgeries, which are drastic steps that can have significant adverse consequences to the patient and often do not work in any event.

The present invention is a dental oral appliance for use with patients who suffer with sleep disorders, to reduce or eliminate snoring and to open the airway for a sleeping individual who suffers with obstructive sleep apnea.

SUMMARY OF THE INVENTION

The present invention is a dental oral appliance, for use with patients who suffer with sleep disorders, to reduce or eliminate snoring and to open the airway for a sleeping individual who suffers with obstructive sleep apnea. The appliance also opens the airway in an awake individual, whose tongue partially blocks/obstructs the airway thereby increasing the airflow in and out and allows more relaxed fuller breathing. This is accomplished as the tongue is trained by the patient wearing the appliance at night to re-position itself forward and up. The appliance typically covers the lower teeth and has an open center where the tongue sits. In the preferred embodiment, the portion of the appliance that covers the lower teeth is custom fit for the specific patient. It is preferred that the appliance fits snuggly on the lower teeth to secure the appliance within the mouth.

There is a transverse strip that extends from the lower right molars to the lower left molars that pushes the tongue upward and forward, thereby breach the airway. In the preferred embodiment, the strip is substantially U-shaped thereby forming a substantial breach therein. It is further preferred that the strip comprises a downward slope. The breach allows the tongue some freedom of movement so that the user can more easily swallow saliva.

The present invention can be modified with a ramp on the front so that, when the user closes his or her mouth, the upper front teeth hit it and are forced forward creating mandibular advancement in a single arch appliance. This additionally aids in further alleviating snoring. Another function of the ramp is as a discluding element to free the muscles of mastication during sleep. This is extremely helpful when treating patients that have temporomandibular joint (TMJ) dysfunction and Myofascial Pain Dysfunction (MPD). These patients' symptoms can be worsened by treatment with traditional Mandibular Advancement Appliances but, because of the ramp functioning as a discluding device, they can be more easily and successfully treated.

The dental appliance can comprise a single piece of material. However, it is possible to have the mouth piece (the portion engaging the lower teeth) and the tongue restraining device be separate pieces. The reason for this design is that the size of everyone's mouth and tongue is different. Therefore the position of the "U" in terms of anterior-posterior, as well as angulation in a vertical plane, needs to have the ability to move to fit each person. By having the "U" as a separate member, it can be attached with a ratchet-type hinge for vertical angulation as well as a sliding-slot mechanism for the anterior-posterior adjustment. Other connection methods known to those of skill in the art can be used as well.

Over time, as the tongue is trained to stay in position during sleep, the device can be adjusted in increase forward positioning of the tongue. After the tongue is fully trained to stay in position, some patients will no longer need to wear the device on a daily basis to avoid snoring.

For a patient who does not have lower molars or who is missing too many lower teeth to secure the device adequately, the dental appliance can be designed for the upper teeth, incorporating aspects of the present invention such as the anterior ramp and an adjustable strip to restrain and reposition the tongue forward.

BRIEF DESCRIPTION OF THE DRAWINGS

The above and other objects and advantages of the present invention will be apparent upon consideration of the following detailed description, taken in conjunction with the accompanying drawings, in which reference characters refer to like parts throughout, and in which.

DETAILED DESCRIPTION OF THE INVENTION

Figure 1:
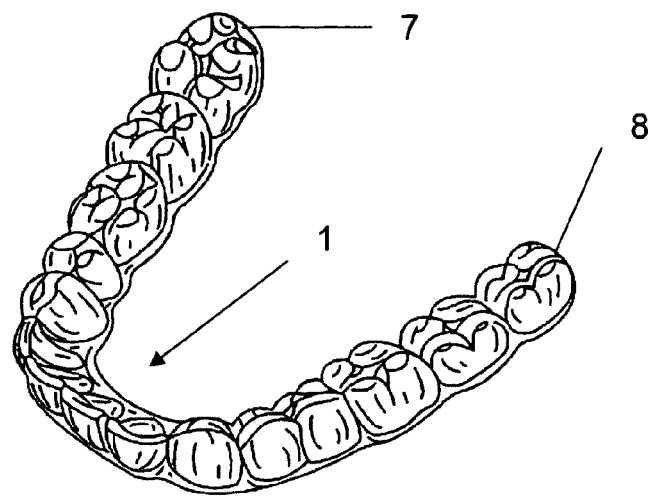
FIG. 1 illustrates an exemplary securing means.

FIG. 1 illustrates an exemplary securing means 1 or base. The securing means shown is acrylic that is molded to fit securely over the lower teeth of the patient. Materials other than acrylic can be used as are known to those with skill in the art. Other types of bases can be utilized in the invention. For example, the base might secure to the upper teeth only or both the upper and the lower teeth. The base shown in FIG. 1 has a right end 7 and a left end 8. For the particular patient for whom the base was molded, the right end 7 is located at the posterior side of the last molar on the right and the left end 8 is located at the posterior side of the last molar on the left. It is preferred that the base is specially molded to fit snuggly over the lower teeth of the patient so that the appliance is better secured when in the mouth.

Figure 2:
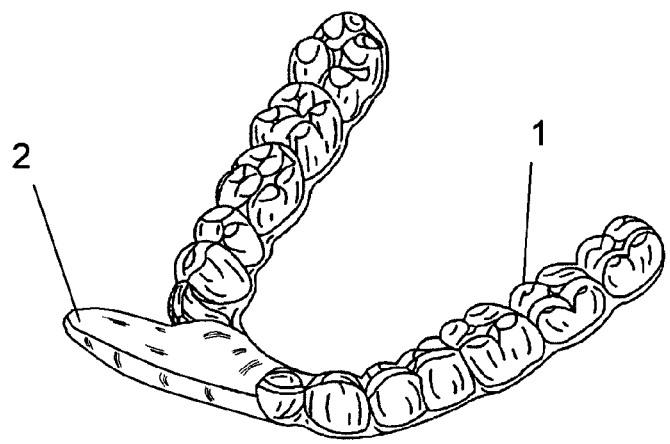
FIG. 2 shows the securing means with a front ramp formed thereon.

FIG. 2 shows the base of FIG. 1, except that a front ramp 2 has been formed on the front of the securing means 1. In the embodiment shown, the front ramp 2 is also formed of acrylic, although other materials can be used. It is also possible to form the base 1 and front ramp 2 simultaneously as a single piece of material, including plastic, acrylic or otherwise. The front ramp 2 extends forward from the anterior portion of the base at an upward angle. When the dental appliance is inserted into position within the mouth, the front ramp forces the lower jaw forward providing mandibular advancement. This helps to alleviate snoring and sleep apnea. In the preferred embodiment, from the bottom of the front of the base, the bottom of the front ramp rises at about a 45 degree angle. It is preferred that that angle is between 40 and 60 degrees. From the top of the front of the base, the top of the front ramp rises at about a 30 degree angle. It is preferred that that angle is between 25 and 45 degrees. For comfort, it is preferred that the ramp is tapered and that is rounded without sharp edges. If the base is secured to the upper teeth, the ramp will need to be angled differently.

Figure 3:
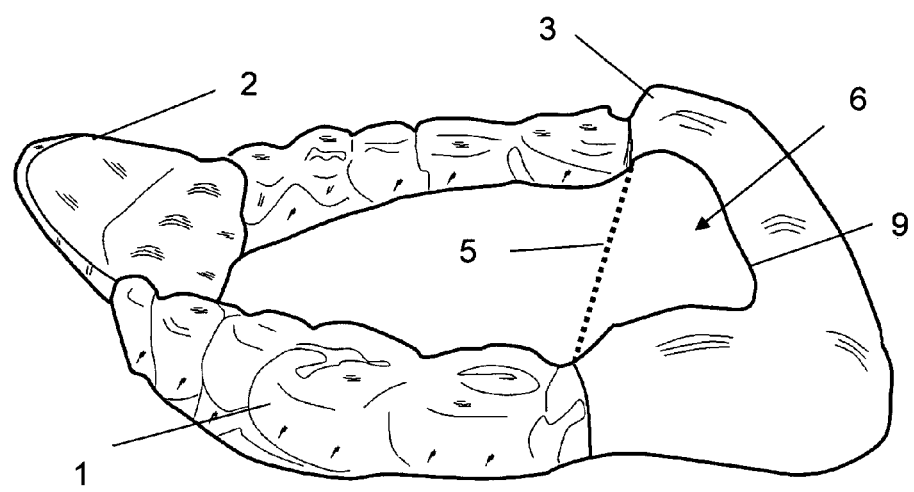
FIG. 3 is a dental appliance according to the present invention.

FIG. 3 shows an exemplary dental appliance according to the present invention. The dental appliance includes the base 1 and the front ramp 2. Extending from the ends of the base 1 is a tongue restraining device 3. When the dental appliance is positioned in the patient's mouth, the tongue restraining device keeps the tongue from falling back, thereby keeping it from blocking the airway. It also will then be moved forward during future visits, bringing the tongue with it to a more forward and upper position. This keeps the airway open and prevents/reduces the number of apneic events (the number of times the tongue falls back and blocks the airway for at least 10 seconds). The tongue restraining device, by positioning the tongue anteriorly/forward and superiorly/up, significantly opens the airway.

In the preferred embodiment, the tongue restraining device is substantially U-shaped and comprises a downward slope. Because the tongue restraining device is U-shaped, a substantial breach is formed therein between the points where the tongue restraining device connects to the base. In FIG. 3, there is an imaginary dashed line 5 illustrating the boundary of the opening 6 formed by the breach within the tongue restraining device. The imaginary dashed line 5 extends from one end of the "U" to the other. More specifically, the opening 6 is formed by the anterior surface 9 of the tongue restraining device. The purpose of the opening 6 is to allow movement of the tongue within the opening 6 so that it is easier for the patient to swallow saliva.

It is possible for the base 1 and tongue restraining device 3 to be formed simultaneously from a single piece of material (e.g. acrylic or other plastic). It is possible to form the base 1 and the tongue restraining device 3 from a material (such as an acrylic) that can be reheated and remolded. This allows the medical practitioner to readjust the tongue restraining device 3 for patient comfort or otherwise. Materials that are commonly used to make moldable mouth guards can be used for this purpose.

It is also possible for the base 1 and the tongue restraining device 3 to be formed separately and later connected together. In one embodiment, the base 1 and the tongue restraining device 3 are connected by an adjustable connection means such as a ratchet mechanism that allows the position of the tongue restraining device 3 to be adjusted. It is preferred that the adjustable connection means allows the tongue restraining device 3 to be lengthened and/or raised/lowered pivotally with respect to the base 1. By having the "U" as a separate member, it can be attached with a ratchet-type hinge for vertical angulation as well as a sliding-slot mechanism for the anterior-posterior adjustment.

Various types of adjustment means known to those skilled in the art can be utilized to allow length and/or pivotal adjustment of the tongue restraining device. Examples of such adjustment means are described in the following US Patents: U.S. Pat. No. 7,415,912 (adjustable components (300 and 400 shown on in the figure on the front page) can be lengthened and shortened with locking screws in slots); U.S. Pat. No. 7,399,288 (adjusting rod to lengthen and shorten neck brace); U.S. Pat. No. 7,384,406 (adjustable-length strut); U.S. Pat. No. 7,377,779 (means to adjust posts); U.S. Pat. No. 7,320,672 (means to adjust angular extension); U.S. Pat. No. 7,166,132 (means to pivotally adjust bone prosthesis); U.S. Pat. No. 7,156,654 (means to lengthen orthodontic appliance); U.S. Pat. No. 7,037,287 (adjustable pivot mechanism for knee brace (see FIG. 6)); U.S. Pat. No. 6,964,566 (adjustment means for lengthening dental oral appliance (see FIG. 9)); U.S. Pat. No. 6,960,175 (adjustment means for pivot in leg brace (see FIGS. 2 and 3)); U.S. Pat. No. 6,926,363 (mechanism for adjusting angle of hinge); U.S. Pat. No. 6,796,951 (mechanism for pivotal adjustment (see FIG. 6)); U.S. Pat. No. 6,783,361 (length in dental appliance adjusted by jack screw controlled by a ratchet); U.S. Pat. No. 6,739,277 (length adjustment mechanism (see FIG. 2)); U.S. Pat. No. 6,656,144 (mechanism for pivotal joint); U.S. Pat. No. 6,629,841 (pivot adjustment mechanism (see FIG. 5)); U.S. Pat. No. 6,523,492 (length adjustment mechanism); U.S. Pat. No. 6,413,232 (pivot adjustment member (see FIGS. 4 and 5); and U.S. Pat. No. 6,383,156 (range of motion hinge with an adjustable length strut (see FIGS. 2A through 8). The complete specification of each patent listed in the previous sentence is incorporated herein by this reference as though set forth in full.

In the preferred practice, the tongue restraining device will be lengthened and pivoted downward as the tongue is trained to stay in good position. This can be accomplished in a number of ways, as discussed above. For example, a plurality of appliances can be manufactured at one time for the patient (typically, three to seven). The base will be the same for each appliance (specially molded according to the lower teeth of the patient). However, the tongue restraining devices will get progressively longer with a more downward slope. The first appliance will have a relatively short tongue restraining device that slopes slightly downward from the base connection points. After the patient has gotten use to the new appliance and the tongue is partially trained, the practitioner can then give the patient the second appliance. The tongue restraining device on the second appliance will be somewhat longer and will have a more downward slope from the base connection points. This process will continue until the tongue restraining device keeps the tongue in a completely correct posture.

The same type process can be accomplished by fabricating new appliances as they are needed. Also, an adjustable appliance, as described above, can be used for this purpose. The number of adjustments required will vary depending on the patient's ability to tolerate the appliance and the changes. Typically, the number of adjustments will be from three to seven. However, 10 or more adjustments might be required.

It should be noted that a dental appliance according to the present invention can also comprise a base and a front ramp but not a tongue restraining device. It is also possible for a dental appliance according to the present invention to comprise a base and a tongue restraining device but not a front ramp.

Figure 4:
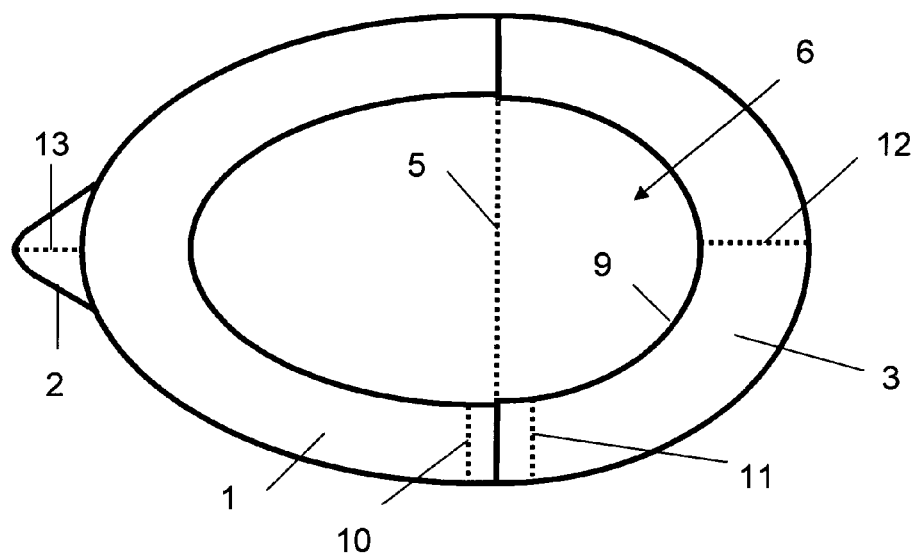
FIG. 4 shows an abstract version of the dental appliance viewed from above.

FIG. 4 provides an abstract version of the dental appliance viewed from above (top view). The abstract version includes the base 1, the front ramp 2, the tongue restraining device 3, and the opening 6 within the tongue restraining device. The purpose of FIG. 4 is to permit discussion of the possible dimensions of the appliance's components. In the example shown in FIG. 4, the length of the imaginary dashed line 5 is about 4 centimeters. Imaginary dashed line 10 is the width of base 1 near the left end. This is about 14 millimeters. This length is due directly to the width of the last left molar of the patient.

Imaginary dashed line 11 is the width of the tongue restraining device proximate to the base. Various sizes are possible. For example, the length of imaginary dashed line 11 might be 15 millimeters or it might be 8 millimeters. This width depends on what room is needed for the tongue to move within the opening 6 and the need for the stability of the tongue restraining device.

Imaginary dashed line 12 is the width of the tongue restraining device at the center. The length of imaginary dashed line 12 can also vary according to what is required to accommodate movement of the tongue within the opening 6 and for patient comfort. Typically, the length of imaginary dashed line 11 will be greater than the length of imaginary dashed line 12. The length of imaginary dashed line 12 might be something like 4 or 5 millimeters.

Imaginary dashed line 13 is the length that the front ramp 2 juts out from the base 1. This might be something like 7 or 8 millimeters.

There is no exact way to determine the optimal length of a tongue restraining device. In fabricating an appliance for a new patient, one might measure from the back of the lower teeth to the location where the tongue begins to go downward in the throat. That measurement can be used as the length of the tongue restraining device. As the treatment progresses, the tongue restraining device can be lengthened and the downward slope increased. The greater the downward slope the greater the length can be.

As can be seen in FIG. 4, from a top view, the size of the breach in the tongue restraining device will generally be substantial. Typically, viewed from above, the area of the breach will be greater than the apparent area of the tongue restraining device. In fact, viewed from above, the area of the breach might be more than twice as large as the apparent area of the tongue restraining device. It is preferred that the size of the breach is as large as is possible, while still maintaining the structural integrity of the tongue restraining device and the desired positioning of the tongue.

Figure 5:
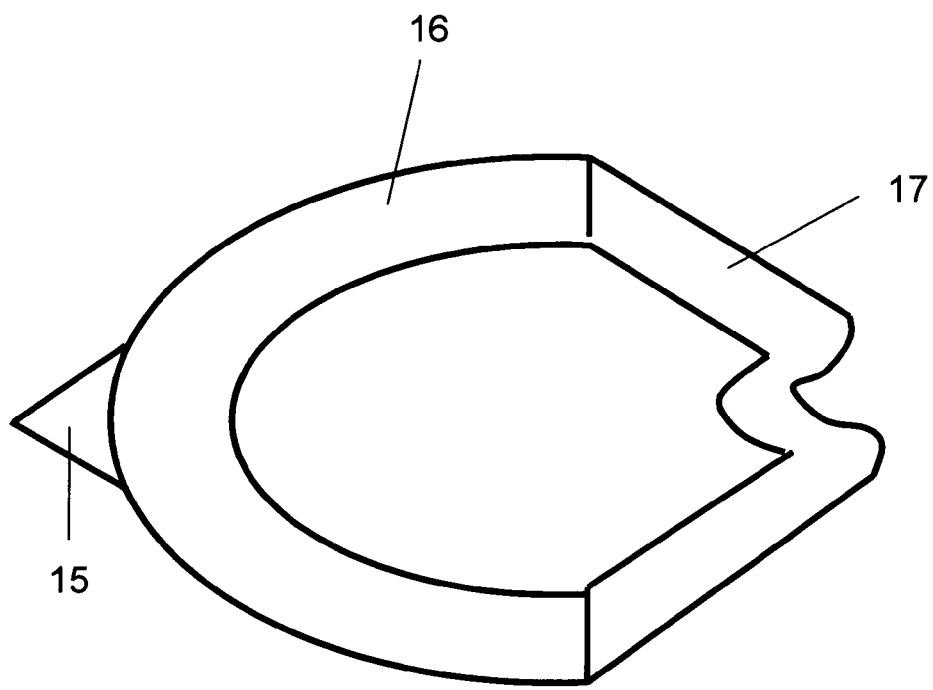
FIG. 5 shows a top view of an abstract version of a dental appliance according to the present invention with a W-shaped tongue restraining device.

It should be noted that shapes other than a U-shape are possible for the tongue restraining device. A rounded W-shape might be used, for instance. In such a configuration, the anterior surface forms an opening within the tongue restraining device to allow for movement of the tongue for swallowing but provides an accordion effect that allows the tongue restraining device to be more easily remolded so as to allow the tongue restraining device to be wider or narrower. FIG. 5 shows provides a top view of an abstract version of such a configuration, with a front ramp 15, a base 16 and a tongue restraining device 17.

The invention claimed is:

1. A dental oral appliance to open an airway for a sleeping individual who suffers with snoring or obstructive sleep apnea comprising: a base comprising a means for securing the appliance to a lower teeth of the individual and said base having an upper side, a bottom side, a front end and a rear end; a tongue restraining device connected to the base, wherein said tongue restraining device comprises a transverse strip that extends from a lower right molars to a lower left molar that pushes the tongue upward and forward and an anterior surface that forms a substantial opening within said tongue restraining device to permit movement of the tongue and wherein said transverse strip is substantially U-shaped and said transverse strip has a downward orientation relative to the bottom side of the base; and a ramp projecting upward from the front end of the base, wherein said ramp is configured, when the appliance is secured in a mouth, to force a mandible forward and wherein said ramp comprises a top portion and a bottom portion and said top portion rises at a first angle that is between 25 to 45 degrees and said bottom portion rises at a second angle that is between 40 and 60 degrees, and wherein said first angle is different than said second angle.

2. The appliance of claim 1 wherein the base and tongue restraining device are formed from a single piece of material.

3. The appliance of claim 2 wherein said material comprises plastic.

4. The appliance of claim 2 wherein said material comprises acrylic.

5. The appliance of claim 2 wherein the tongue restraining device is heatable and repositionable.

6. The appliance of claim 1 wherein the base and the tongue restraining device comprise separate pieces.

7. The appliance of claim 6 wherein the tongue restraining device is connected to the base by an adjustable connection device.

8. The appliance of claim 1 wherein the tongue restraining device has a top side and, when the tongue restraining device is viewed from the top, the opening formed by the anterior surface is greater in area than a surface of the tongue restraining device.

9. The appliance of claim 1 wherein the base is custom fit for the individual.

10. The appliance of claim 1 wherein the tongue restraining device is custom fit for the individual.

* * * * *